United States Patent [19]
Gafvelin et al.

[11] Patent Number: 4,840,785
[45] Date of Patent: Jun. 20, 1989

[54] MAMMAL INTESTINAL HORMONE PRECURSOR AND ITS USE

[75] Inventors: Guro Gafvelin, Stockholm; Mats Carlquist, Sundbyberg; Viktor Mutt, Solna, all of Sweden

[73] Assignee: Kabigen AB, Stockholm, Sweden

[21] Appl. No.: 934,449

[22] PCT Filed: Mar. 7, 1986

[86] PCT No.: PCT/SE86/00100
§ 371 Date: Nov. 10, 1986
§ 102(e) Date: Nov. 10, 1986

[87] PCT Pub. No.: WO86/05495
PCT Pub. Date: Sep. 25, 1986

[30] Foreign Application Priority Data
Mar. 11, 1985 [SE] Sweden ................................. 8501203

[51] Int. Cl.$^4$ ..................... A61K 49/00; A61K 37/24; C07K 7/32
[52] U.S. Cl. ......................................... 424/9; 514/12; 530/309; 530/324
[58] Field of Search ................... 530/309, 324; 514/12; 436/501; 424/9

[56] References Cited
FOREIGN PATENT DOCUMENTS
2025466 12/1970 Fed. Rep. of Germany .
2323187 11/1973 Fed. Rep. of Germany .

OTHER PUBLICATIONS
Hubel, Gastroenterology, vol. 62, No. 2, pp. 318–341 (1972).
Carlquist et al., Journal of Chromatography, vol. 296, pp. 143–151 (1984).
Gafvelin et al., FEBS vol. 184, No. 2, pp. 347–352 (5/1985).
Mutt et al., "On the Assay of Secretin", Ark. Kem., vol. 15, pp. 63–68 (1959).
Roth, "Fluorescence Reaction, for Amino Acids", Analytical Chemistry, vol. 43, pp. 880–882 (1971).
Koop et al., "Purification and Characterization of a Unique Isozyme of Cytochromo P–450 from Liver Microsomes of Ethanol–Treated Rabbits", J. Bio. Chem., vol. 257, pp. 8472–8480 (1982).
Heinrikson et al., "Amino Acid Analysis by Reverse--Phase High-Performance Liquid Chromatography: Precolumn Derivatization with Phenylisothiocyanate", S.C. Analytical Biochem., vol. 136, pp. 65–74 (1984).
Dimaline et al., "Multiple Immunoreactive Forms of Vasoactive Intestinal Peptide in Human Colonic Mucosa", Gastroenterology, vol. 75, pp. 387–392 (1978).
Said et al., "Isolation from Porcine–Intestinal Wall of a Vasoactive Octacosapeptide Related to Secretin and to Glucagon", Eur. J. Biochem., vol. 28, pp. 159–204 (1972).
Mutt et al., "Structure of Porcine Secretin–The Amino Acid Sequence", Eur. J. Biochem., vol. 15, pp. 513–519 (1970).
Carlquist et al., "Isolation and Amino Acid Sequence of Bovine Secretin", FEBS Letters, vol. 127, No. 1, pp. 71–74 (1981).

Primary Examiner—Delbert R. Phillips
Assistant Examiner—Christina Chan
Attorney, Agent, or Firm—Burns, Doane, Swecker & Mathis

[57] ABSTRACT

A mammal intestinal hormone precursor having the following peptide structure: His-Ser-Asp-Gly-Thr-Phe-Thr-Ser-Glu-Leu-Ser-Arg-Leu-Arg-L-M-Ala-Arg-Leu-Gln -Arg-Leu-Leu-Gln-Gly-Leu-Val-Gly-N-O, wherein L is Glu or Asp, M is Gly or Ser, and N and O are selected from Lys and Arg; compositions containing such precursor and a method of stimulating pancreatic secretion.

15 Claims, 2 Drawing Sheets

MAMMAL INTESTINAL HORMONE PRECURSOR AND ITS USE

The present invention relates to a mammal intestinal hormone precursor related to the hormone secretin which stimulates pancreatic secretion.

Secretin is an intestinal hormone formed by the mucosa of the upper portion of the small intestine, which stimulates the secretion of water and bicarbonate from the pancreas. The structure of porcine secretin has been known for some time and it has been isolated from porcine intestine and has been found to be constituted by a peptide composed of 27 amino acid residues (Mutt, V., Jorpes, J.E. and Magnusson, S. (1970) Eur.J.Biochem., 15, 513–519). Moreover, it has been found that bovine and porcine secretins are identical but that they are marked different from chicken secretin (Carlquist, M., Jörnvall, H. and Mutt, V. (1981) FEBS Lett., 127, 71–74). The C-terminal amino acid residue of secretins (valine in porcine/bovine, methionine in chicken) is, as in many other hormonally active peptides, amidated.

In accordance with the present invention variant forms of secretins which are not amidated at its C-terminal residue but instead have a C-terminal residue of glycine have now been found. These variants which can be considered as proforms are precursors to the natural secretins possess high secretin-like bioactivity.

Thus, according to the present invention there is provided a mammal intestinal hormone precursor having the following peptide structure: His-Ser-Asp-Gly-Thr-Phe-Thr-Ser-Glu-Leu-Ser-Arg-Leu-Arg-L-M-Ala-Arg-Leu-Gln-Arg-Leu-Leu-Gln-Gly-Leu-Val-Gly-N-O, wherein L is Glu or Asp, M is Gly or Ser, and N and O are selected from Lys and Arg.

It can be seen from this structure that it contains 30 amino acid residues corresponding to a natural secretin molecule extended by three amino acid residues.

In the hormone precursor corresponding to the human secretin L is Glu and M is Gly, whereas in the non-human counterpart L is Asp and M is Ser.

In regard to the C-terminal amino acid residues it is preferred that one of N and M is Lys and the other one is Arg.

BRIEF DESCRIPTION OF THE DRAWINGS

In the drawigns

Figure 1:
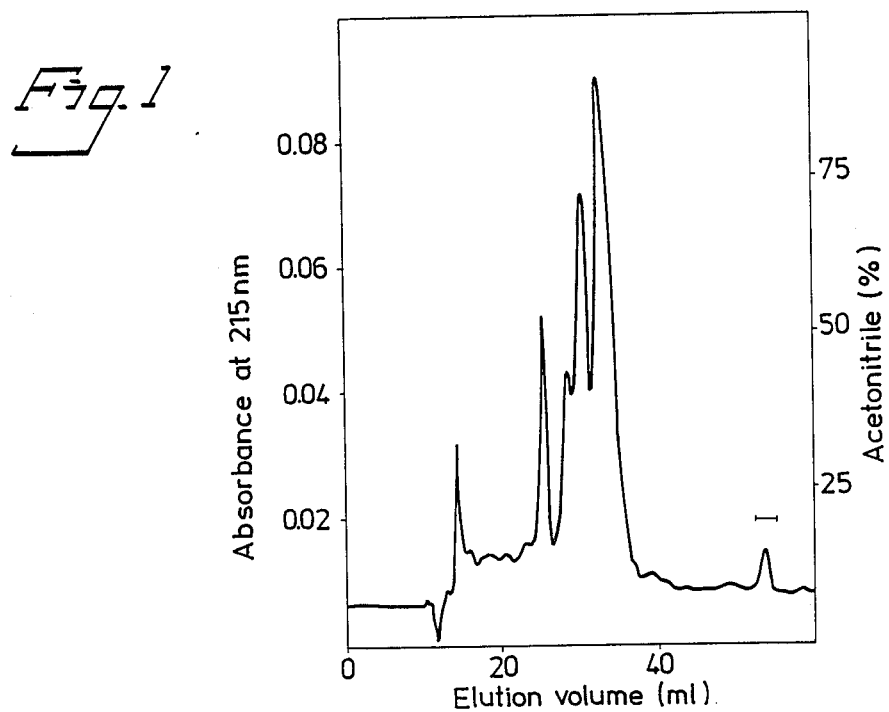
FIG. 1 is a reverse-phase chromatogram involving a first step purification of the secretin variant or precursor.

It has been found that the secretin precursors according to this invention are at least as potent as natural secretins in stimulating the secretion of bicarbonate by the pancreas of the anesthetized cat (Mutt, V. and Soderberg, U. On the assay of secretin. Ark.Kem. 15, 63–68, 1959).

In the instant disclosure the abbreviations used for characterizing the amino acids and their residues are the traditional ones as found for example in the textbook Organic Chemistry, second edition, Ralph J. Fessenden & Joan S. Fessenden, Willard Grant Press, Boston, Mass., pages 852 and 853.

In the same way as the known natural secretins find diagnostic uses the secretin precursors according to this invention are highly useful in determining pancreatic and gallbladder functions. According to this aspect of the invention a composition for diagnostic use in this respect comprises an effective diagnostic amount of the secretin precursor of this invention in combination with a carrier which does not interfere with the diagnostic procedure used.

The secretin precursor of this invention is in addition therapeutically useful in that it stimulates pancreatic secretion in mammals if administered in a suitable manner. According to this aspect of the invention a composition for such use is provided comprising an effective therapeutic amount of the secretin precursor of the invention in combination with a non-toxic, pharmaceutically acceptable carrier. In this context the invention also covers a method of treating gastrointestinal disorders comprising administering a therapeutically effective amount of the secretin precursor of this invention or a composition of this invention on a patient to be treated.

The present invention thus includes within its scope pharmaceutical compositions, which comprise the mammal intestinal hormone precursor according to this invention in association with a pharmaceutically acceptable carrier. In clinical practice the compositions of the present invention will normally be administered parenterally due to the fact that being a peptide the hormone precursor is sensitive to biologically active environments. Oral or rectal administration may, however, be conceivable using compositions of the slow release type making it possible for the active ingredient to reach the site of primary interest, namely the small intestine.

Preparations according to the invention for the preferred parenteral administration includes sterile aqueous or non-aqueous solutions, suspensions or emulsions. Examples of non-aqueous solvents or suspending media are propylene glycol, vegetable oils, such as olive oil, and injectible organic esters, such as ethyl oleate. These compositions may also contain adjuvants, such as preserving, wetting, emulsifying and dispersing agents. They may be sterilized, for example, by filtration through a bacteria-retaining filter, by incorporation of sterilizing agents in the composition, by irradiation or by heating. They may also be manufactured in the form of sterile solid compositions, which can be dissolved in a sterile injectible medium immediately before use. As well as the more customary intravenous and intramuscular routes the composition may also be administered by intra-articular injection.

The percentages of active ingredient in the compositions of the invention may be varied as long as they constitute a proportion such that a suitable dosage for the desired stimulatory effect on the pancreas is obtained. Obviously several unit dosage forms may be administered at about the same time. Generally, the compositions should contain from about 0.1% to about 80% by weight of active ingredient.

The dose employed depends upon the desired stimulatory effect, the route of administration and the duration of the treatment. The hormone precursor of this invention may be administered each day or, according to the wishes of the medical practitioner, less often e.g. weekly.

This invention also covers a method of stimulating pancreatic secretion in a patient suffering from gastrointestinal disorder, this method comprises administering to the patient an amount of the hormone precursor or the composition of the invention sufficient to combat such disorder.

The invention will be further illustrated below in an example describing the isolation and characterization of a secretin precursor of this invention.

EXAMPLE

The starting material

The upper part of porcine intestine was boiled, frozen and minced. The resulting powder was extracted with 0.5 M acetic acid and the peptides were adsorbed on alginic acid. Then elution with 0.2 M HCl and precipitation with NaCl were performed. The resulting eluate was gelfiltered on Sephadex G25 (Pharmacia Fine Chemicals) in 0.2 M acetic acid. Extraction was carried out with methanol and soluble materials were precipitated with ether. The resulting solution was gelfiltered on Sephadex G25 (Pharmacia Fine Chemicals) in 0.2 M acetic acid. The resulting solution was subjected to ion exchange chromatography on CM-cellulose and elution was then carried out with 12.5 mM phosphate buffer at a pH of 8. With regard to details of the procedure see Said, S.I. and Mutt, V. Isolation from porcine-intestinal wall of a vasoactive octacosapeptide related to secretin and to glucagon. *Eur.J.Biochem.* 28, 199–204, 1972.

The eluate was further subjected to two additional CM-chromatographies. In the first one the elution was carried out in a 0.02 M phosphate buffer at pH 6.4 with a salt gradient of 0–0.3 M NaCl. A fraction eluting at about 0.15 M NaCl was further chromatographed on a second CMC column eluted with a stepwise gradient at pH 8 in $NH_4HCO_3$ at different concentrations. The fraction referred to here as the "starting material" was eluted with 0.04 M $NH_4HCO_3$ from this column. The starting material was further purified on high performance liquid chromatography (HPLC)

HPLC

Reverse phase HPLC was carried out on a /μBondapak $C_{18}$ column (7.8×300 mm) or a LKB Ultropac TSK ODS-120T column (3.9×300 mm) with 0.12% trifluoroacetic acid (TFA) in water and 0.1% TFA in acetonitrile as mobile phases. Ion exchange chromatography was performed on a LKB Ultropac TSK535 CM-column (7.5×150 mm) with 0.02 sodium phosphate buffer at pH 6.4 and a NaCl-gradient of from 0 to 0.3 M NaCl. Both reverse phase and ion exchange HPLC were carried out on an instrument from Waters Associated.

Biological activity

The biological activity was measured by the ability to stimulate the secretion of alkali in the pancreatic juice in the anesthetized cat (Mutt, v. and Söderberg, U. On the assay of secretin. *Ark.Kem.* 15, 63–68, 1959). The sample was compared to a secretin standard with an established activity of 3500 units per mg.

Proteolytic fragmentation

The peptide was digested with TPCK-treated trypsin for 6 h or TLCK-treated chymotrypsin for 4 h in 1% $NH_4HCO_3$, pH 8 at room temperature. The ratio of peptide to enzyme was 50:1 by weight. The enzymes were purchased from Worthington (trypsin) and Merck (chymotrypsin). The proteolytic fragments were separated by reverse phase HPLC on a /μBondapak $C_{18}$ column (7.8 x 300 mm) or a LKB Ultropac TSK ODS-120T column (3.9×300 mm) with 0.12% trifluoroacetic acid (TFA) in water and 0.1% TFA in acetonitrile as mobile phases. Ion exchange chromatography was performed on a LKB Ultropac TSK535 CM-column (7.5×150 mm) with 0.02 sodium phosphate buffer at pH 6.4 and a NaCl-gradient of from 0 to 0.3 M NaCl. Both reverse phase and ion exchange HPLC were carried out on an instrument from Waters Associated.

Biological activity

The biological activity was measured by the ability to stimulate the secretion of alkali in the pancreatic juice in the anesthetized cat (Mutt, V. and Soderberg, U. On the assay of secretin. *Ark.Kem.* 15, 63–68, 1959). The sample was compared to a secretin standard with an established activity of 3500 units per mg.

Proteolytic fragmentation

The peptide was digested with TPCK-treated typsin for 6 h or TLCK-treated chymotrypsin for 4 h in 1% $NH_4HCO_3$, pH 8 at room temperature. The ratio of peptide to enzyme was 50:1 by weight. The enzymes were purchased from Worthington (trypsin) and Merck (chymotrypsin). The proteolytic fragments were separated by reverse phase HPLC on a /μBondapak $C_{18}$ column as described above. The gradients used were, for tryptic fragments, 0–40% acetonitrile in TFA for 40 minutes at a flow rate of 1 ml per minute and, for chymotrypsic fragments, 10–25% acetonitrile in TFA for 30 minutes at a flow rate of 1 ml per minute.

Amino acid composition analysis

Hydrolysis was carried out in evacuated tubes containing 6M HCl with 0.1% β-mercaptoethanol at 110° C. for 24 h. All hydrolysates were analyzed in a Beckman 121 amino acid analyzer except the tryptic digests which were analyzed in a Waters Assoc. amino acid analysis system using precolumn derivitization with o-phthalaldehyde (OPA) (Roth, N. Analytical Chemistry 43, 880–882, 1971).

Identification of free arginine

The tryptic digestion mixture was treated with PITC (Koop, D.R., Morgan, E.T., Tarr, G.E. and Coon, M.J. *J.Biol.Chem.* 257, 8472–8480, 1982) to form the phenylthiocarbamyl derivative of the fragments formed during tryptic digestion of the secretin variant. The mixture of the tryptic peptides and any free PTC-amino acid was then run on a Spherisorb $C_{18}$ column (3/μ) in a HPLC-system for separation of PTC-amino acids. The system used was as described by Heinrikson and Meredith (Heinrikson, R.L. and Meredith, S.C. *Analytical Biochem.* 136, 65–74, 1984).

RESULTS

During the purification of VIP and a search for variant forms of it (Dimaline, R. and Dockray, G.J. Multiple immunoreactive forms of vaso-active intestinal peptide in human colonic mucosa. *Gastroenterology* 75, 387–392, 1978) a certain fraction was observed to have a secretin- rather than a VIP-like bioactivity.

Figure 2:
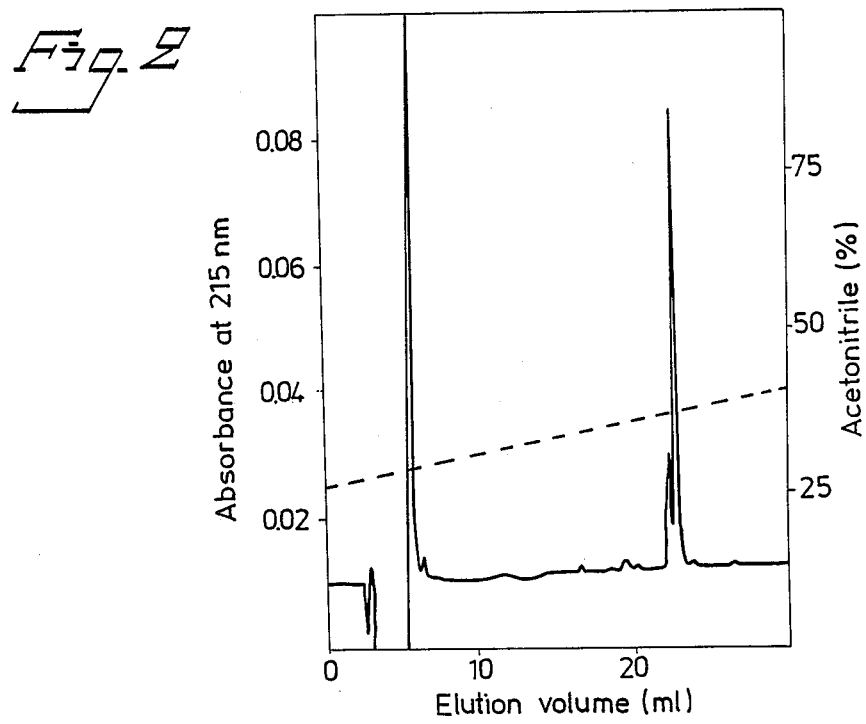
FIG. 2 is a chromatogram from the second step purification of the secretin variant or precursor after an ion exchange HPLC-step.
Figure 3:
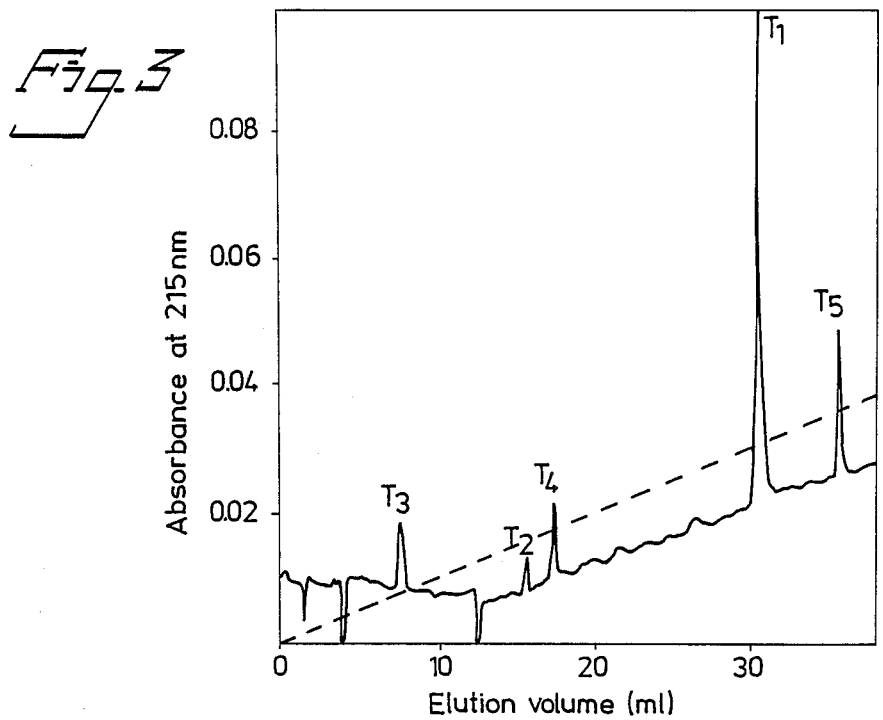
FIG. 3 is a chromatogram of the tryptic fragments of the purified peptide and of secretin.
Figure 4:
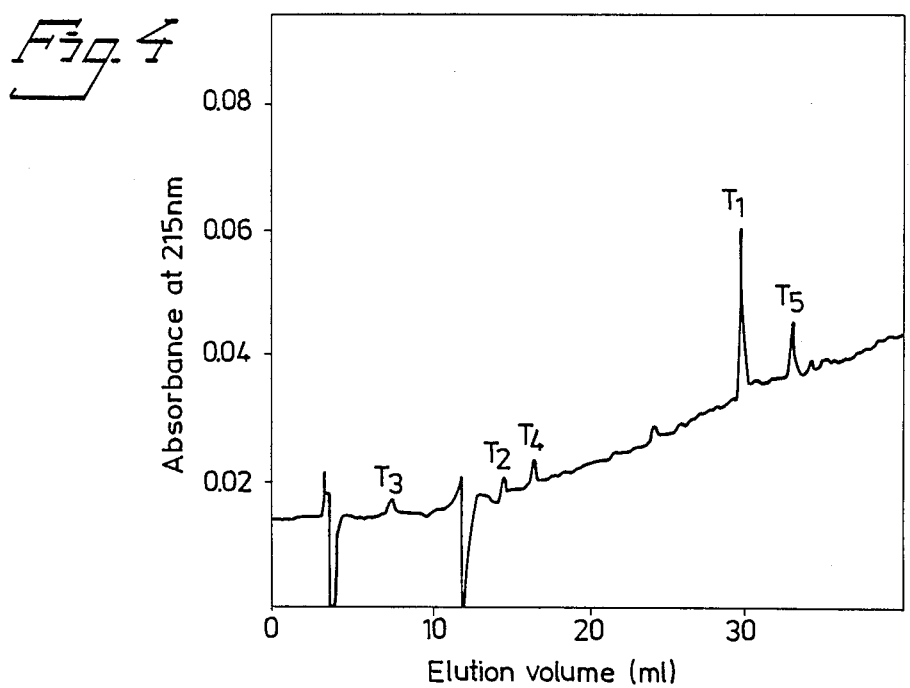
FIG. 4 is another chromatogram of the tryptic fragments of the purified peptide and of secretin.

The final purification of the secretin variant or precursor from the starting material was obtained by three HPLC chromatographies. The first HPLC-step was a reverse phase chromatography on a /μBondapak $C_{18}$ column using a gradient of 32–38% acetonitrile in 0.12% TFA, 30 minutes at a flow rate of 2 ml per minute. The chromatogram is shown in FIG. 1. The active fraction was further subjected to an ion exchange HPLC-step on a LKB Ultropac CM column eluted with a gradient of 0.12 to 0.3M NaCl in a 0.02 M phosphate buffer pH 6.4 for 15 minutes and isocratic elution at 0.3 M NaCl in the same buffer for another 15 minutes. THe flow rate was 1 ml per minute. Desalting by reverse phase HPLC using a LKB Ultropac ODS column also gave some purification (FIG. 2) and the isolated peptide was considered to be pure after this step. Active fractions were identified with the bioassay for secretin (described under "The Starting Material") throughout the purification procedure The total amino acid composition of the intact peptide is shown in Table 1. Comparison of this amino acid compostion position to that of secretin indicates that the isolated peptide differs from porcine secretin by containing a Lys residue and one additional residue each of Arg and Gly. To check if the purified peptide is a variant form of secretin, tryptic digestion of it was carried out and the fragments obtained were separated on reverse phase HPLC. The chromatograms of the tryptic fragments of the purified peptide and of secretin are shown in FIGS. 3 and 4. Only one fragment eluted at different positions in the two chromatograms. This fragment corresponds to the C-terminal fragment T5 as shown by the amino acid composition. Each tryptic fragment of the isolated peptide was hydrolyzed and subjected to total amino acid composition analysis. The amino acid compositions of the tryptic peptides are shown in Table 3. The C-terminal fragment of the peptide, $T_5$, contains an extra Gly and a Lys residue as compared to the corresponding fragment of secretin, while the other fragments ($T_4$-$T_5$) are identical with the secretin fragments. Chymotryptic degradation of secretin and of the isolated peptide was carried out in parallel and led in both cases to numerous fragments. With one exception each fragment of the peptide appeared to be identical to a fragment of secretin and vice versa.

The amino acid compositions of the two nonidentical fragments was determined (Table 2). That of the secretin fragment was $Gly_1$, $Glx_1$, $Leu_1$, $Val_1$, unequivocally showing that it represented the C-terminal Gln-Gly-Leu-Val-NH$_2$ sequence of secretin. That of the polypeptide fragment was $Arg_1$, $Gly_2$, $Glx_1$, $Leu_1$, $Lys_1$, $Val_1$, suggesting the sequence Gln-Gly-Leu-Val-Gly-Lys-Arg. Consequently the findings suggested that the polypeptide consisted of secretin extended C-terminally with Gly-Lys-Arg. If so, free arginine should be split from it on tryptic degradation and this was also shown to be the case; a tryptic digest was derivatized with PITC (Koop, D.R., Morgan, E.T., Tarr, G.E. amd Coon, M.J. *J.Biol.Chem.* 257, 8472-8489, 1982) and applied to an HPLC-system for the detection of PTC-amino acids. All five tryptic peptide derivatives and free PTC-arginine were indeed detected.

The above data show that the isolated polypeptide of the invention is a variant form of secretin with a C-terminal extension by Gly-Lys-Arg. This is in good agreement with the knowledge that in peptide hormone precursor proteins a glycine residue followed by paired basic residues usually represents amidation and cleavage signals, respectively.

The pure secretin precursor was tested for bioactivity in the secretin bioassay described above. As shown in Table 3, secretin-Gly-Lys-Arg is about 1.5 times more potent than secretin itself.

It is to be noted that the invention is not limited to the specific details and features of the examples dedescribed above and that modifications can be made to the polypeptide structure without deviating from the inventive idea. Thus, the invention is not limited otherwise than according to the scope of the appended patent claims.

| Amino acid | Secretin variant | Secretin |
|---|---|---|
| Lys | 1.1 (1) | — |
| His | 1.3 (1) | 1 |
| Arg | 4.9 (5) | 4 |
| Asx | 2.1 (2) | 2 |
| Thr | 1.8 (2) | 2 |
| Ser | 3.3 (4) | 4 |
| Glx | 3.0 (3) | 3 |
| Gly | 3.0 (3) | 2 |
| Ala | 1.2 (1) | 1 |
| Val | 1.0 (1) | 1 |
| Leu | 6.0 (6) | 6 |
| Phe | 1.0 (1) | 1 |
| Total | 30 | 27 |

| Amino acid | $T_1$ | $T_2$ | $T_3$ | $T_4$ | $T_5$ | Chymotryptic fragment |
|---|---|---|---|---|---|---|
| Lys | — | — | — | — | 1.0(—) | 0.9(—) |
| His | 0.8(1) | — | — | — | — | — |
| Arg | 0.8(1) | 0.9(1) | 0.8(1) | 0.8(1) | — | 0.9(—) |
| Asx | 1.3(1) | — | 1.3(1) | — | — | — |
| Thr | 2.0(2) | — | — | — | — | — |
| Ser | 2.8(3) | — | 0.9(1) | — | — | — |
| Glx | 1.4(1) | — | — | 1.2(1) | 1.3(1) | 1.2(1) |
| Gly | 1.0(1) | — | — | — | 1.4(1) | 2.0(1) |
| Ala | — | — | 1.0(1) | — | — | — |
| Val | — | — | — | — | 1.3(1) | 0.9(1) |
| Leu | 1.0(1) | 1.1(1) | — | 1.0(1) | 3.0(3) | 1.1(1) |
| Phe | 0.9(1) | — | — | — | — | — |
| Total | 12 | 2 | 4 | 3 | 6 | 4 |

We claim:

1. A mammal intestinal hormone precursor having the following peptide structure: His-Ser-Asp-Gly-Thr-Phe-Thr-Ser-Glu-Leu-Ser-Arg-Leu-Arg-L-M-Ala-Arg-Leu-Gln-Arg-Leu-Leu-Gln-Gly-Leu-Val-Gly-N-O, wherein L is Glu or Asp, M is Gly or Ser, and N and O are selected from Lys and Arg.

2. The hormone precursor of claim 1, wherein L is Glu and M is Gly.

3. The hormone precursor of claim 1, wherein L is Asp and M is Ser.

4. The hormone precursor of claim 1, wherein N is Lys and O is Arg.

5. The hormone precursor of claim 1, wherein N is Arg and O is Lys.

6. The hormone of claim 2, wherein N is Lys and O is Arg.

7. A composition for use in stimulating pancreatic secretion in mammals or for diagnostic use in determining pancreatic or gallbladder function, comprising an effective therapeutic amount to stimulate pancreatic secretion or an effective diagnostic amount for use in determining pancreatic or gallbladder function of the hormone precursor of claim 1 in combination with a non-toxic and non-interfering carrier therefore.

8. A composition for use in stimulating pancreatic secretion in man, comprising an effective therapeutic amount of the hormone precursor of claim 2 in combination with a non-toxic carrier therefore.

9. A method of stimulating pancreatic secretion in a patient suffering from gastrointestinal disorder, which comprises administering to the patient an amount of the hormone precursor of claim 1 or the composition of claim 7 or 8 sufficient to combat such disorder.

10. A method of stimulating pancreatic secretion in a patient suffering from gastrointestinal disorder, which comprises administering to the patient an amount of the hormone precursor of claim 2 sufficient to combat such disorder.

11. A method of stimulating pancreatic secretion in a patient suffering from gastrointestinal disorder, which comprises administering to the patient an amount of the hormone precursor of claim 3 sufficient to combat such disorder.

12. A method of stimulating pancreatic secretion in a patient suffering from gastrointestinal disorder, which comprises administering to the patient an amount of the hormone precursor of claim 4 sufficient to combat such disorder.

13. A method of stimulating pancreatic secretion in a patient suffering from gastrointestinal disorder, which comprises administering to the patient an amount of the hormone precursor of claim 5 sufficient to combat such disorder.

14. A method of stimulating pancreatic secretion in a patient suffering from gastrointestinal disorder, which comprises administering to the patient an amount of the composition of claim 7 sufficient to combat such disorder.

15. A method of stimulating pancreatic secretion in a patient suffering from gastrointestinal disorder, which comprises administering to the patient an amount of the composition of claim 8 sufficient to combat such disorder.

* * * * *